United States Patent [19]
Nordquist et al.

[11] Patent Number: 5,840,978
[45] Date of Patent: Nov. 24, 1998

[54] PROCESS FOR PREPARING ETHYLIDENE BISFORMAMIDE

[75] Inventors: Andrew Francis Nordquist, Whitehall; Francis Peter Petrocelli, Blandon; Robert Krantz Pinschmidt, Jr.; Yin Pang Tsui, both of Allentown, all of Pa.

[73] Assignee: Air Products and Chemicals, Inc., Allentown, Pa.

[21] Appl. No.: 26,907

[22] Filed: Mar. 5, 1993

[51] Int. Cl.⁶ .................................................. C07C 233/03
[52] U.S. Cl. ........................... 564/159; 564/160; 564/215
[58] Field of Search .................................... 564/159, 160, 564/215

[56] References Cited

U.S. PATENT DOCUMENTS

| | | | |
|---|---|---|---|
| 4,176,136 | 11/1979 | Brenzel | 564/159 |
| 4,490,557 | 12/1984 | Dawson et al. | 564/159 |
| 4,906,777 | 3/1990 | Pinschmidt et al. | 564/275 |

FOREIGN PATENT DOCUMENTS 232245  10/1991  Japan .

*Primary Examiner*—Shailendra Kumar
*Attorney, Agent, or Firm*—Keith D. Gourley

[57] ABSTRACT

This invention describes an integrated process for making ethylidene bisformamide in high yield wherein water, which is formed as a reaction by-product, is readily removed from the reaction product mixture without adversely affecting the efficiency of the overall process. The process contemplates isolating the reaction zone from the separation zone and comprises circulating a stream of formamide through a reaction zone containing a solid acidic catalyst and a separation zone; introducing acetaldehyde into the circulating stream of formamide to form a reaction mixture and contacting the reaction mixture with the solid acidic catalyst under reaction conditions sufficient to form a product mixture comprising ethylidene bisformamide and water; and separating water from the product mixture in the separation zone to form a water-depleted product mixture containing ethylidene bisformamide.

20 Claims, No Drawings

5,840,978

PROCESS FOR PREPARING ETHYLIDENE BISFORMAMIDE

TECHNICAL FIELD OF THE INVENTION

The present invention relates to a catalytic process for preparing ethylidene bisformamide from formamide and acetaldehyde.

BACKGROUND OF THE INVENTION

Ethylidene bisformamide is used to prepare various poly(vinylamines) which are used to manufacture numerous pharmaceuticals and water treatment chemicals. Typically, ethylidene bisformamide is cracked to form N-vinylformamide monomer which is polymerized to form poly(N-vinylformamide). The resulting polymer is then hydrolyzed to form the desired poly(vinylamine). Several methods are known for producing ethylidene bisformamide.

U.S. Pat. No. 4,490,557 issued Dec. 25, 1984 to Dawson et al. discloses a process for preparing ethylidene bisformamide wherein dry acetaldehyde and formamide are reacted in the presence of an acidic catalyst and an ammonia scavenger such as acetic anhydride. Ethylidene bisformamide is recovered from the reaction mixture via wiped film evaporation. Suitable acidic catalysts include formic acid, acetic acid, mineral acids or acidic ion exchange resins. The patent teaches the feed stocks and the catalysts should be dried prior to use in order to minimize the presence of water in the reaction zone. Water generated during the reaction can also be trapped by acetic anhydride. Other steps to minimize water include blanketing the reaction zone with a dry gas.

U.S. Pat. No. 4,906,777 issued Mar. 6, 1990 to Pinschmidt, Jr., et al., discloses a process for making ethylidene bisformamide wherein formamide and acetaldehyde, in a mole ratio of at least 3:1, and a high concentration of formic acid are reacted under conditions sufficient to form ethylidene bisformamide. Water formed in the reaction one can be distilled out as a binary or terniary azeotrope with one or more co-solvents such as toluene or hexane.

Japanese Patent Application No. 2-32245, filed Feb. 13, 1990, and laid open Oct. 22, 1991 discloses a process for making ethylidene bisformamide wherein N-(α-hydroxyethyl)formamide and formamide are subjected to a dehydrocondensation reaction in the presence of an acidic catalyst such as an ion exchange resin. N-(α-hydroxyethyl)formamide is stated to be a required starting material The product mixture formed in the reaction zone consists of N-(α-hydroxyethyl)formamide, formamide, ethylidene bisformamide and water in the presence of the acidic catalyst. Water can be stripped from the reaction mixture at elevated temperature.

Researchers continue their quest to discover improved processes for preparing ethylidene bisformamide wherein water can be conveniently removed from the product mixture while minimizing formation of reaction by-products which can diminish catalyst activity.

SUMMARY OF THE INVENTION

This invention relates to a process for making ethylidene bisformamide which comprises circulating a stream of formamide through a reaction zone containing a solid acid catalyst and a separation zone; introducing acetaldehyde into the circulating stream of formamide to form a reaction mixture and contacting the reaction mixture with the solid acidic catalyst under reaction conditions sufficient to form a product mixture comprising ethylidene bisformamide and water; and separating water from the product mixture in the separation zone to form a water-depleted product mixture containing ethylidene bisformamide. The water-depleted product mixture can be recirculated into the reaction mixture for further processing.

The claimed process contemplates separating the reaction zone from the separation zone such that the temperature of the reaction zone and the temperature of the separation zone can be independently controlled. According to the process, water can be removed from the reaction mixture without using large amounts of formic acid solvent or using a cosolvent to form a water/cosolvent azeotrope. For example, water can be removed from the product mixture by any conventional separation scheme capable of selectively separating water from the other respective components by employing a selective membrane, a selective adsorbent or by distillation techniques, preferably vacuum flashing.

Applicants have discovered that superior conversion of acetaldehyde to ethylidene bisformamide occurs when process conditions are controlled such that the product mixture formed in the reaction zone comprises less than about 30 mol % acetaldehyde, preferably 0.2 to 5 mol % acetaldehyde. Water present in the enumerated product mixture can be separated efficiently in the separation zone by vacuum flashing to form a water-depleted product mixture which can then be recirculated into the reaction mixture for further processing.

DETAILED DESCRIPTION OF THE INVENTION

The present invention relates to an integrated process for producing ethylidene bisformamide in high yield wherein water, which is formed as a reaction by-product, is readily removed from the reaction product mixture without adversely affecting the efficiency of the overall process. Applicants' process for making ethylidene bisformamide utilizes at least two zones, namely a reaction zone and a separation zone.

More specifically, the process comprises circulating a stream of formamide through the reaction zone containing a solid acidic catalyst and the separation zone; introducing acetaldehyde into the circulating stream of formamide to form a reactant mixture and passing the reactant mixture over the solid acidic catalyst residing in the reaction zone; contacting the reactant mixture with the solid acidic catalyst residing in the reaction zone under reaction conditions sufficient to form a product mixture comprising ethylidene bisformamide and water; and separating water from the product mixture in the separation zone. Finally, the water-depleted product mixture is recirculated into the circulating stream of formamide for further reaction.

Applicants' process contemplates separating the reaction zone from the separation zone such that the temperature of the reaction zone and the temperature of the separation zone can be independently controlled. Hydrolysis of formamide to ammonia is minimized resulting in extended catalyst life. Moreover, water formed during the process is removed from the product mixture without using large amounts of formic acid solvent or using a cosolvent to form a water/cosolvent azeotrope.

In a preferred embodiment of the invention, Applicants have discovered that superior conversion of acetaldehyde to ethylidene bisformamide occurs when the process conditions are controlled such that the product mixture formed in the reaction zone comprises less than about 30 mol % acetaldehyde, preferably 0.2 to 5 mol % acetaldehyde. Water present in the enumerated product mixture can then be separated efficiently in the separation zone by controlling the temperature in the separation zone from 40° to 120° C. and separating water from the product mixture by vacuum flashing to form a water stream and a water depleted product mixture containing ethylidene bisformamide. The water-depleted product mixture can be recirculated into the reaction mixture for further reaction.

The claimed process effectively limits hydrolysis of formamide which occurs when water formed during the reaction reacts with formamide to form formic acid and various ammonium salts. These hydrolysis products deactivate the catalyst and decrease conversion of formamide to ethylidene bisformamide. Applicants' decoupling of the reaction zone from the separation zone allows the reaction to be conducted under conditions favorable to minimizing the formation of undesirable products while conducting the separation step at process temperatures which maximize the efficiency for separating water from the reaction products.

Prior art processes typically conduct the reaction and separation steps in a single zone wherein a single temperature regime is employed for reacting the starting materials to form ethylidene bisformamide and separating water from the product mixture containing ethylidene bisformamide. Consequently, the operating temperature neither maximizes conversion to product nor optimizes the amount of water removed from the product mixture.

In the first step of the process, a stream of formamide is circulated through a reactor comprising at least two zones, a first zone for conducting the reaction, referred to as the reaction zone, and a second zone for separating water from the product mixture formed in the reaction zone, referred to as the separation zone. The temperature of the circulating formamide is typically maintained at a temperature ranging from 5° to 40° C. prior to introducing acetaldehyde into the process such that the temperature within the reaction zone can be controlled within an optimum range.

Suitable reactors equipped with a reaction zone include conventional reactors which can be operated batchwise or in a continuous mode. A variety of reactor configurations can be employed to produce ethylidene bisformamide in a batch-type operation. For example, formamide and a solid acidic catalyst may be initially charged to a stirred-batch slurry reactor. Preferably, a fixed-bed reactor operated in a full recycle mode is utilized wherein the enumerated catalysts reside in the reactor. The fixed-bed reactor is thus a reaction zone where the circulating formamide and acetaldehyde to be added react in the presence of the solid acidic catalyst to form ethylidene bisformamide and water.

In the next step of the process, acetaldehyde is introduced into the circulating stream of formamide to form a reaction mixture and the reaction mixture is contacted with the solid acidic catalyst within the reaction zone under reaction conditions sufficient to form a product mixture comprising ethylidene bisformamide and water. Acetaldehyde is preferably added incrementally into the circulating stream to control the reaction exotherm. Acetaldehyde is typically introduced into the circulating stream of formamide at a rate sufficient to maintain the temperature in the reaction zone at between 5° and 40° C. The optimum rate can be readily deduced by one of ordinary skill in the art to which this invention pertains. Typical mol ratios of formamide to acetaldehyde range from 2:1 to 10:1 and preferably range from 3:1 to 4:1.

The temperature in the reaction zone is desirably maintained at or below ambient temperature during the addition of acetaldehyde to minimize transferring acetaldehyde from the liquid phase to the vapor phase and to ensure good contact of acetaldehyde with the catalyst. Since the reaction zone is decoupled from the separation zone, the reaction temperature can be conveniently controlled to reduce acetaldehyde self condensation, which is an undesirable side reaction. Suitable reaction conditions to be maintained in the reaction zone include a temperature ranging from 40° to 100° C., preferably 50° to 80° C.

Solid acidic catalysts suitable for practicing the process include heterogeneous strong acids, such as ion exchange resins which may contain acidic groups such as carboxylic acid and sulfonic acid groups. The term, acidic, does not necessarily mean that a pH value of less than 7 is obtained when the catalyst is contacted with water, but refers to nature of functional groups residing on the resin. The amount of solid acidic catalyst used in the present invention typically ranges from 0.1 to 100 mole %, preferably 1–20 mole % with reference to acetaldehyde.

Examples of suitable resins include (1) resins derived from monohydric and polyhydric phenols and aldehydes which are further modified by reaction with sulfurous acid, sulfites and sulfur dioxide and (2) sulfonated polystyrene which is crosslinked with agents such as divinylbenzene. Examples of such materials are gel and macroreticular resins which are commercially available from Rohm and Haas Company under trademarks XN1010, Amberlyst 15, Amberlite 200, Amberlite IR 118, 120, 122, IRC 50, Duolite C-3, C-20, C-20X10, CC-33 and C-25D; from Permutit Company (England) as Zeocarb 225, 215 and 266; from Permutit Company (USA) as Permutit Q, Q 110 and Q 210; and from Bio-Rad Laboratories as BioRex 40 and 70 and as AG-50-X8 and AG-MP-50. Preferred ion exchange resins include sulfonic acid functional ion exchange resins such as Amberlyst-15® from Rohm and Haas Company. Other comparable ion exchange, whether available commercially or obtainable by standard preparations, can be used as well as mixtures of two or more resins.

The reaction product is conveniently separated from the solid acidic catalyst residing in the reaction zone offering a significant advantage over conventional acidic catalysts such as mineral acids which are miscible with the product mixture. In the event that the reaction zone comprises a slurry reactor, then the product mixture and the catalyst can be separated by passing the reaction mixture through a filter, a settling basin or a like solid-liquid separation means.

In the final step of the process, water is separated from the product mixture in a separation zone which is isolated from the reaction zone to form a water-depleted product mixture containing ethylidene bisformamide and a water-enriched stream which is removed from the process. Water can be separated from the product mixture by conventional separation means such as selective adsorption, azeotropic distillation and membrane separation. With respect to selective adsorption, the equilibrium adsorption isotherm of water-formamide mixtures can be readily determined at 30° C. on any commercially available zeolite 3A. The equilibrium adsorption capacity of zeolite 3A corresponds to 12 wt % water uptake at a water composition of 2–4 wt %, while formamide adsorption is not observed.

In a preferred embodiment, water is separated from the product mixture by heating the product mixture within the separation zone to a temperature ranging from 40° to 120° C. and vacuum flashing the product mixture to form a water-enriched stream and a water-depleted product mixture comprising ethylidene bisformamide. The water-depleted product mixture can be recirculated into the reaction zone for further reaction while the water-enriched stream is typically discarded. The vacuum flashing is typically conducted at a temperature ranging from 60° to 120° C. and a pressure ranging from 0 to 200 mbar although other conditions can be used to similar advantage.

The following examples are provided to further describe the claimed invention and are not to be construed as limiting the scope of the appended claims.

EXPERIMENTAL

The process of the present invention can be practiced utilizing a variety of processing schemes. The following examples are provided to demonstrate the claimed invention. A catalyst such as Amberlyst-15® ion-exchange resin is packed into three 2-inch ID, 4-ft long stainless steel tubes situated within a cylindrical outer shell located in the reactor zone. An ethylene glycol/water mixture is either cooled or heated externally and circulated through the outer shell of the reactor to control the reactor temperature during the reaction. Internal thermocouples are situated along the center axis of each reactor tube such that the axial temperature gradients are maintained at less than 5° C., and that no significant tube-to-tube temperature variations occur.

The reaction mixture is circulated through the system using two constant-speed gear pumps (maximum flowrate of 2.0 GPM) connected to a recirculating loop. The circulation rate is typically maintained at 0.7–1.0 GPM. Circulation rate is measured by rotameters situated directly downstream of both pumps. Formamide is initially charged into the system at a temperature ranging from 5° to 40° C. Acetaldehyde is then incrementally fed to the stream of circulating formamide to form a reaction mixture. The acetaldehyde is typically added over a one hour period from a 20-liter feed vessel pressurized to 60–80 psig with nitrogen.

The reaction is allowed to proceed according to the desired reaction conditions. For example, following a period of 80 minutes after the start of acetaldehyde addition, the reactor reached a temperature of 40° C. and the circulating fluid was transferred to a separation zone wherein the pressure in the separation zone was reduced to 25 mbar.

Water removal by vacuum flashing was performed separate from the reactor. The reactor effluent is preheated to a temperature 0°–80° C., preferably 5°–20° C. higher than the reactor temperature, and flashed across an orifice into a disengaging section. Liquid effluent from the disengaging section is cooled, and returned to the reactor inlet During normal operation, the preheated stream temperature is raised to a typical final value of 80°–120° C. as the reactor temperature is raised to a typical final value of 60°–80° C. Typical flash pressure at the typical preheat temperature is 0–200 mbar, preferably 10–50 mbar (absolute).

Referring to the Table, examples 1 through 3 illustrate results obtained when no vacuum flashing is utilized. In examples 4–8, water was removed from the reactor effluent by vacuum-flash prior to returning the mixture to the reactor inlet. Catalyst loading was calculated by dividing the equivalents of acid in the reactor by the total moles of acetaldehyde fed to the system. The formamide/acetaldehyde ratio was likewise calculated by dividing the moles of formamide initially charged to the mix vessel by the total moles of acetaldehyde fed to the system. Ethylidene bisformamide yield was calculated by dividing the moles of ethylidene bisformamide in the final product by the moles of acetaldehyde remaining in the system after flashing. Catalyst loading (shown as H+/acetaldehyde ratio in Table 1) was calculated by dividing the equivalents of acid in the reactor by the total moles of acetaldehyde fed to the system.

The benefit of flashing to remove water during the production of ethylidene bisformamide is significant. Examples 1, 2, and 3, run without flashing to remove water during the production of ethylidene bisformamide provide substantially poorer conversion to ethylidene bisformamide. In these examples, ethylidene bisformamide yield was calculated by dividing the moles of ethylidene bisformamide in the final product by the moles of acetaldehyde initially fed, because, without flashing, no acetaldehyde was removed.

Examples 4 through 8 used similar catalyst loadings although the product mixture was vacuum flashed to remove water prior to returning the water-depleted product mixture to the reactor inlet. This flashing provided a greater than 10% increase in ethylidene bisformamide yield as compared to the examples in which water was not removed by vacuum flashing. A higher ethylidene bisformamide yield is obtained even at reduced catalyst loadings when water is removed from the system via vacuum flashing.

TABLE

| Example | 1 | 2 | 3 | 4 | 5 | 6 | 7 | 8 |
|---|---|---|---|---|---|---|---|---|
| Flash used? | no | no | no | yes | yes | yes | yes | yes |
| H+/AcH (mol/mol) | 0.124 | 0.124 | 0.124 | 0.124 | 0.124 | 0.100 | 0.050 | 0.075 |
| FAM/AcH (mol/mol) | 4.1 | 3.5 | 3.4 | 4.0 | 4.5 | 4.0 | 3.0 | 3.0 |
| Run duration (min) | 225 | 210 | 215 | 240 | 255 | 270 | 380 | 350 |
| Flash start time (min) | — | — | — | 85 | 80 | 85 | 135 | 185 |
| Flash end time (min) | — | — | — | 190 | 255 | 270 | 380 | 350 |
| AcH add duration (min) | 52 | 56 | 59 | 58 | 60 | 60 | 90 | 160 |
| Initial temp (°C.) | 20 | 20 | 22 | 20 | 20 | 20 | 20 | 20 |
| Initial hold duration (min) | 55 | 60 | 60 | 60 | 66 | 60 | 110 | 160 |
| First ramp duration (min) | 22 | 60 | 60 | 75 | 20 | 25 | 30 | 25 |
| Intermediate temp (°C.) | 40 | — | — | — | 40 | 35 | 30 | 30 |
| Intermediate hold duration (min) | 0 | — | — | — | 0 | 15 | 15 | 0 |
| Second ramp duration (min) | 73 | — | — | — | 70 | 110 | 155 | 105 |
| Final temp (°C.) | 60 | 60 | 60 | 60 | 60 | 59 | 60 | 54 |

TABLE-continued

| Example | 1 | 2 | 3 | 4 | 5 | 6 | 7 | 8 |
|---|---|---|---|---|---|---|---|---|
| Final hold duration (min) | 75 | 90 | 95 | 105 | 105 | 60 | 70 | 60 |
| BIS yield (%) | 83 | 80 | 82 | 94 | 96 | 96 | 88 | 94 |
| AcH conversion before flash (Mol %) | — | — | — | 93 | 92 | 90 | 86 | 90 |

The present process eliminates the need to dry feed stocks and catalysts prior to conducting the process because water can be efficiently removed during the process. Moreover, the present process overcomes the need to add acetic anhydride as a water scavenger and reduces formation of unwanted byproducts caused when acetic anhydride reacts with other components in the reaction mixture.

The invention is not limited to the foregoing description. Variations and modifications will become apparent to those skilled in the art without departing from the spirit and scope or the invention.

We claim:

1. A process for making ethylidene bisformamide comprising the steps of:
   (a) circulating a stream of formamide through a reaction zone and a separation zone wherein the reaction zone contains a solid acidic catalyst;
   (b) introducing acetaldehyde into the circulating stream of formamide to form a reaction mixture and contacting the reaction mixture with the solid acidic catalyst under reaction conditions sufficient to form a product mixture comprising ethylidene bisformamide and water;
   (c) separating water from the product mixture in the separation zone to form a water-depleted product mixture containing ethylidene bisformamide; and
   (d) recirculating the water-depleted product mixture into the reaction zone.

2. The process of claim 1 wherein ethylidene bisformamide is separated from the water-depleted product mixture.

3. The process of claim 1 wherein the solid acidic catalyst is an ion exchange resin.

4. The process of claim 3 wherein the ion exchange resin is a sulfonated styrene-divinylbenzene resin.

5. The process of claim 1 wherein the circulating stream of formamide according to step (a) is maintained at a temperature ranging from 5° to 40° C. prior to conducting step (b).

6. The process of claim 5 wherein acetaldehyde is introduced into the circulating stream of formamide at a rate sufficient to maintain the temperature in the reaction zone between 5° and 40° C.

7. The process of claim 1 wherein the reaction conditions sufficient to form the product mixture include a temperature ranging from 40° to 100° C.

8. The process of claim 1 wherein the separating of water from the product mixture is effected by contacting the product mixture with a selective membrane capable of forming the water-depleted product mixture.

9. The process of claim 1 wherein the separating of water from the product mixture is effected by contacting the product mixture with an adsorbent selective toward water to form the water-depleted product mixture.

10. The process according to claim 9 wherein the adsorbent is Zeolite 3A.

11. The process according to claim 1 wherein the separating of water from the product mixture is effected by vacuum flashing to form the water-depleted product mixture.

12. A process for making ethylidene bisformamide comprising the steps of:
   (a) circulating a stream of formamide through a reaction zone containing a solid acidic catalyst and a separation zone;
   (b) introducing acetaldehyde into the circulating stream of formamide to form a reactant mixture and passing the reactant mixture over the solid acidic catalyst residing in the reaction zone;
   (c) contacting the reactant mixture with the solid acid catalyst residing in the reaction zone under reaction conditions to form a product mixture comprising ethylidene bisformamide, water and up to about 30 mol % acetaldehyde;
   (d) heating the product mixture within the separation zone to a temperature ranging from 40° to 120° C. and separating water from the product mixture by vacuum flashing to form a water-enriched stream and a water-depleted product mixture and recirculating the water-depleted product mixture into the reaction mixture according to step (b).

13. The process of claim 12 wherein ethylidene bisformamide is separated from the water-depleted product mixture.

14. The process according to claim 12 wherein the solid acidic catalyst is an ion exchange resin.

15. The process according to claim 14 wherein the ion exchange resin is a sulfonated styrene-divinylbenzene resin.

16. The process according to claim 12 wherein the circulating stream of formamide according to step (a) is maintained at a temperature ranging from 5° to 15° C. prior to conducting step (b).

17. The process according to claim 12 wherein acetaldehyde is introduced into the circulating stream of formamide according to step (b) at a rate sufficient to maintain the reaction zone temperature between 5° and 40° C.

18. The process according to claim 17 wherein the reaction conditions sufficient to form the product mixture include a temperature ranging from 50° to 80° C.

19. The process according to claim 18 wherein the vacuum flashing according to step (d) is conducted at a temperature ranging from 60° to 120° C. and a pressure ranging from 0 to 200 mbar.

20. The process according to claim 18 wherein the vacuum flashing according to step (d) is conducted at a temperature ranging from 80° to 100° C. and a pressure ranging from 0 to 50 mbar.

* * * * *